(12) United States Patent
Whitehead et al.

(10) Patent No.: US 8,105,469 B2
(45) Date of Patent: Jan. 31, 2012

(54) MICROELECTRODE ARRAY

(76) Inventors: Andrew John Whitehead, Surrey (GB); Geoffrey Alan Scarsbrook, Berkshire (GB); Julie Victoria MacPherson, Coventry (GB); Mark Newton, Warwickshire (GB); Patrick Robert Unwin, Warwickshire (GB); William Joseph Yost, III, Brookline, MA (US)

( * ) Notice: Subject to any disclaimer, the term of this patent is extended or adjusted under 35 U.S.C. 154(b) by 543 days.

(21) Appl. No.: 12/282,594

(22) PCT Filed: Mar. 19, 2007

(86) PCT No.: PCT/IB2007/000679
§ 371 (c)(1),
(2), (4) Date: Feb. 12, 2009

(87) PCT Pub. No.: WO2007/107844
PCT Pub. Date: Sep. 27, 2007

(65) Prior Publication Data
US 2009/0152109 A1 Jun. 18, 2009

Related U.S. Application Data

(60) Provisional application No. 60/783,438, filed on Mar. 20, 2006.

(30) Foreign Application Priority Data

Mar. 17, 2006 (GB) .................................. 0605470.4

(51) Int. Cl.
*G01N 27/26* (2006.01)
(52) U.S. Cl. ... 204/409; 204/294; 204/284; 204/290.03; 204/290.15; 204/416
(58) Field of Classification Search .................. 204/294, 204/280, 284, 290.01, 290.03, 290.15, 409, 204/412, 416
See application file for complete search history.

(56) References Cited

U.S. PATENT DOCUMENTS

| 5,512,489 A | * | 4/1996 | Girault et al. ............... 205/777.5 |
| 5,635,054 A | * | 6/1997 | Girault et al. ................. 205/775 |
| 5,739,039 A | * | 4/1998 | Girault et al. ............ 204/403.14 |
| 5,824,494 A | | 10/1998 | Feldberg |

(Continued)

FOREIGN PATENT DOCUMENTS

DE 199 39 011 C1 1/2001

(Continued)

OTHER PUBLICATIONS

Ph. Rychen, et al., "Environmental Sensing Potential With Boron-Doped Diamond Microdisc and Macro-Electrodes", Electrochemical Society Proceedings, Electrochemical Society, vol. 2001-23, XP008035711, pp. 97-107.

(Continued)

*Primary Examiner* — Bruce Bell
(74) *Attorney, Agent, or Firm* — Oblon, Spivak, McClelland, Maier & Neustadt, L.L.P.

(57) ABSTRACT

Microelectrode comprising a body formed from electrically non-conducting material and including at least one region of electrically conducting material and at least one passage extending through the body of non-conducting material and the region of conducting material, the electrically conducting region presenting an area of electrically conducting material to a fluid flowing through the passage in use. An electrochemical cell which includes such a microelectrode is also disclosed.

44 Claims, 6 Drawing Sheets

U.S. PATENT DOCUMENTS

| | | | |
|---|---|---|---|
| 6,020,110 A * | 2/2000 | Williams et al. | 430/315 |
| 7,407,566 B2 * | 8/2008 | Jiang et al. | 204/400 |
| 2005/0029095 A1 * | 2/2005 | Hall et al. | 204/400 |
| 2005/0029125 A1 * | 2/2005 | Jiang et al. | 205/775 |
| 2007/0051625 A1 * | 3/2007 | Pickles et al. | 204/400 |
| 2008/0257730 A1 * | 10/2008 | Jiang et al. | 204/412 |

FOREIGN PATENT DOCUMENTS

| | | |
|---|---|---|
| DE | 102 29 210 A1 | 1/2004 |
| EP | 0 102 042 A2 | 3/1984 |
| EP | 0102042 * | 3/1984 |
| GB | 2 353 363 A | 2/2001 |
| JP | 59-38647 | 3/1984 |
| JP | 5-281180 | 10/1993 |
| JP | 8-207273 | 8/1996 |
| JP | 2002-515603 | 5/2002 |
| JP | 2003-517149 | 5/2003 |
| JP | 2003-303954 | 10/2003 |
| JP | 2004-207272 | 7/2004 |
| JP | 2006-78404 | 3/2006 |
| WO | WO 99/60392 | 11/1999 |
| WO | WO 99/60392 A1 | 11/1999 |
| WO | WO 9960392 * | 11/1999 |
| WO | WO 01/43870 A2 | 6/2001 |
| WO | WO 2005/012894 A1 | 2/2005 |
| WO | WO 2005/090954 A1 | 9/2005 |
| WO | WO 2006/013430 A1 | 2/2006 |

OTHER PUBLICATIONS

Office Action mailed Aug. 19, 2011, in Japanese Patent Application No. 2009-500953 (English language translation).

* cited by examiner

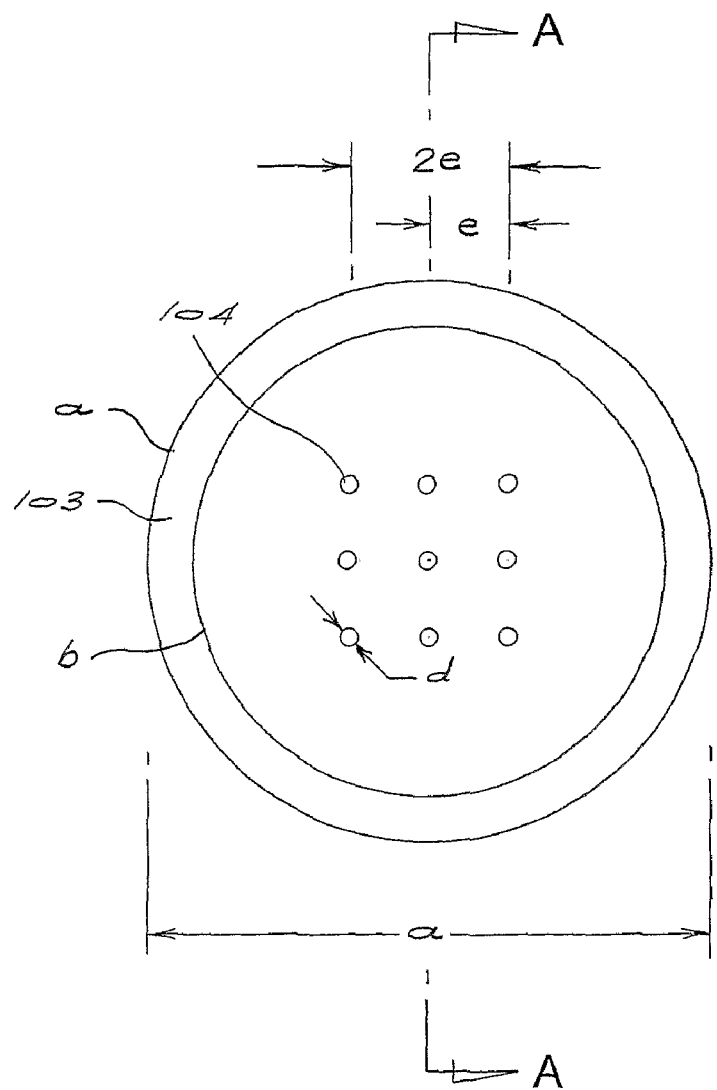
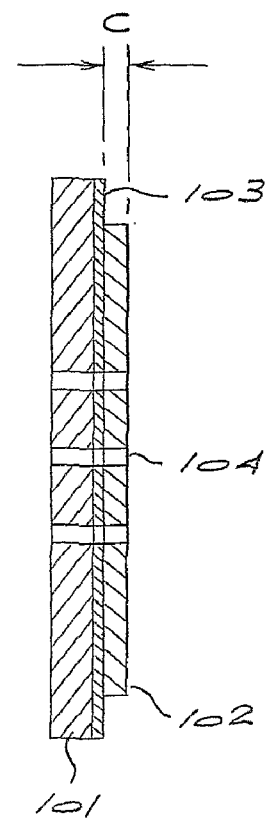
Fig. 8A
Fig. 8B

MICROELECTRODE ARRAY

BACKGROUND OF THE INVENTION

This invention relates to microelectrodes, in particular diamond microelectrodes.

Microelectrodes, amongst other applications, are used in electrochemical applications to characterise fluids, such as liquids or gases. Such electrochemical measurements can be qualitative or comparative, or they may be quantitative. Quantitative measurements generally require that the system is amenable to mathematical modelling, and in both cases it is desirable that the signal to noise in the system is maximised and that as much information as possible is extracted from the system (see Feeney et al, Electroanalysis, vol 12 (2000), page 677). Both of these objectives can best be achieved by using small electrodes, i.e. microelectrodes, such that the configuration approximates to a semi-spherical or three dimensional diffusion model rather than either a linear or two dimensional diffusional model.

The use of such microelectrodes is well known in the art, and became an active field of research in the late 1970's. Subsequent general development of electronics has provided the tools required to utilise such electrodes efficiently. Typical benefits realised include increased temporal resolution, increased current density, decreased sensitivity to solution resistance, and steady state diffusion profiles.

Traditionally, such microelectrodes are arranged as an array presenting contact surfaces that are exposed to the fluid to be analysed. Typically, in order to fabricate such microelectrodes a conductive electrode material, such as a metal, is coated with a non-conducting layer, which is then perforated with one or more apertures to form the microelectrodes which will come into contact with the fluid. In recent times, boron doped CVD diamond has become established as an electrode material, and fabrication of microelectrodes onto a boron doped diamond layer has been reported. Typically such electrodes are a few microns in diameter, fabricated by applying a layer of $Si_3N_4$ or similar non-conductive material to the surface of the diamond and subsequently etching apertures into it to expose the diamond underneath (e.g. P Rychen et al., Electrochemical Society Proceedings, Vol. 23 (2001), pp 97-107). More recently, the present applicant developed a microelectrode comprising a diamond layer formed from electrically non-conducting diamond and containing one or more pins or projections of electrically conducting diamond extending at least partially through the layer of non-conducting diamond and presenting areas of electrically conducting diamond, as disclosed in international patent application WO 2005/012894. The use of an electrode formed solely of diamond provides: (i) exceptionally high resistance to attack by a very wide range of chemicals under a very wide range of conditions, (ii) a wide potential window and (iii) low background currents allowing the devices to be used and remain stable in a wide range of chemically aggressive environments.

However, a two-dimensional diamond microelectrode array ("MEA") such as that described in WO 2005/012894 has a number of drawbacks. For instance, the method of fabrication of the devices is complex and requires precision bulk removal of the boron-doped material to leave the array of pins, a subsequent second deposition step to refill the space between the pins with intrinsic (i.e. non-conductive) diamond, and a final step in which the surface is precision polished to re-expose the tops of the pins. There is also a necessity for the spacing between individual electrodes to be greater than the diffusion length of the species being investigated so that each device can be treated as being independent of all the surrounding devices. The overall signal level may also be low as the density of active sites may be low. Generally the devices also need to operate under conditions where diffusion is the dominant mechanism for species transport (i.e. they need to operate under quiescent conditions).

SUMMARY OF THE INVENTION

According to the present invention, a microelectrode comprises a body formed from electrically non-conducting material, preferably non-conducting diamond, and including at least one region of electrically conducting material, in particular electrically conducting diamond, and at least one passage, preferably an analysis passage, extending through the body of non-conducting material and the region of conducting material, the region of conducting material presenting an area or areas of electrically conducting material to a fluid flowing through the passage in use.

It will be appreciated that three types of passage are contemplated in the present invention; an analysis passage adapted to analyse a fluid flowing through the passage; a simple passage not adapted to analyse a fluid flowing through the passage and an intersecting passage which may or may not be adapted to analyse a fluid flowing through the passage and which intersects a simple passage or an analysis passage. The term 'passage' is intended to refer to any one or more type of passage as hereinbefore described.

The body may include more than one region of electrically conducting material and the analysis passage will pass through the body of electrically non-conducting material and through the regions of electrically conducting material.

The region or regions will generally take the form of a layer or layers.

The microelectrode of the invention may comprise a single analysis passage or may comprise a number of analysis passages arranged in an array, which may be a regular array or an irregular array. The microelectrode may include one or more simple passages.

In particular, the microelectrode of the invention preferably comprises a layered structure of non-conducting material comprising at least two intrinsic (i.e. non-conducting) spaced layers and at least one conducting layer sandwiched between the layers of non-conducting material, with one or more analysis passages formed through the layers in a direction transverse to the layers. In use, the fluid to be monitored is flowed or forced through the analysis passage(s) in the microelectrode and a potential is read out between the conducting layer(s) and a reference electrode elsewhere in contact with the fluid.

Where the body is formed of diamond, it may be in whole or in part single crystal diamond or polycrystalline diamond, and may be natural diamond or synthetic diamond. In the case of synthetic diamond, it can be produced by a high pressure high temperature (HPHT) technique (referred to hereinafter as "HPHT diamond") or by a chemical vapour deposition (CVD) technique (referred to hereinafter as "CVD diamond").

Each analysis passage defines one or more analysis surfaces, each analysis surface including an area or areas of electrically conducting diamond (the "analysis surface(s)"). In many cases the analysis passages are fabricated normal to the generally large planar surfaces of the electrode, although it is also possible for some or all of the analysis passages to be fabricated at angles other than normal to the generally large planar surfaces and for passages to intersect. Intersecting passages, which may also be analysis passages or may be free of analysis regions may combine or separate as viewed in the direction of fluid flow, and may avoid intersection of any of the conducting layers, for example by running essentially in the plane of the layers.

In most circumstances, the analysis passages will all have a circular cross-section and generally be of the same diameter. However, in certain circumstances the analysis passages may be of varying shape or diameter, with the shape or diameter varying either from passage to passage or within a passage or both. Varying the shape or diameter of an analysis passage along its length allows for the velocity of the fluid to be varied and therefore also allows for the time resolution of the electrode to be varied. Different regions of the device, electrically isolated from one another, can thus use different analysis passage designs to optimise the analysis provided in terms of time domain or other parameters.

Likewise, in most circumstances, the intersecting passages will all have a circular cross-section and generally be of the same diameter. However, in certain circumstances the intersecting passages may be of varying shape or diameter, with the shape or diameter varying either from passage to passage or within a passage or both. Varying the shape or diameter of an intersecting passage along its length allows for the velocity of the fluid to be varied and therefore also allows for the time resolution of the electrode to be varied. Different regions of the device, electrically isolated from one another, can thus use different intersection passage designs to optimise the analysis provided in terms of time domain or other parameters.

Varying the passage shape or diameter can also modify the pressure of the fluid, and a diameter change can, for example, be used as a venturi to drive fluid flow and mixing where passages intersect.

The analysis passages through the layered diamond structure are typically tubular and can be closely packed in the body, subject to the requirements of retaining sufficient strength in the device, for example forming a hexagonal array of apertures on the major faces forming the entry and exit faces of the device. Strictly for the invention to work the entry and/or exit apertures of the analysis passages do not need to lie on major faces of the device, and the passages could themselves be curved or contain angles, however, the preferred structure is for the entry and/or exit apertures of the analysis passages to lie on major faces of the device, and preferably for the analysis passages to be essentially straight.

The areas of electrically conducting regions are preferably in electrical connection to one or other external surfaces of the body through which they can be connected to an external circuit, referred to herein as "the contact surface(s)".

The invention provides, according to another aspect, an electrochemical cell which includes a microelectrode of the type described above.

The conductive regions of the diamond may be generated by any method known in the art, but are preferably produced by the addition of dopant elements. Doping can be achieved by implantation, but is preferably achieved by incorporation of the dopant element during synthesis of the diamond, e.g. during synthesis of the diamond by chemical vapour deposition (CVD). The preferred method of making the CVD diamond conductive is by the addition of boron during the synthesis process, although other dopants such as phosphorus or sulphur may also be used.

When the conductive regions comprise boron doped CVD diamond, the boron concentration within the CVD diamond layer is preferably greater than about 0.01 ppm (parts per million), preferably greater than about 0.1 ppm, preferably greater than about 1 ppm, preferably greater than about 10 ppm, preferably greater than about 100 ppm, preferably greater than about 200 ppm, preferably greater than about 500 ppm, preferably greater than about 1000 ppm.

When the conductive regions comprise boron doped CVD diamond, the boron concentration within the CVD diamond layer is preferably less than about 20000 ppm, preferably less than about 15000 ppm, preferably less than about 10000 ppm.

When the conductive regions comprise boron doped CVD diamond, the boron concentration within the CVD diamond layer is preferably between 1000 ppm and 15000 ppm The boron concentration of a region of boron doped diamond can be measured using secondary ion mass spectroscopy (SIMS). Preferably multiple measurements of the boron concentration are made and the arithmetical average of the concentrations taken. Preferably the number of measurements comprising the multiple measurements is at least 5.

Preferably the dopant concentration is uniform through the conductive layer or layers. In this context, the term "uniform" is intended to refer to the dispersion of dopant when viewed over the analysis surfaces of an individual conducting layer.

More specifically, it is preferred that the uniformity is such that the concentration of dopant atoms, as measured for example by SIMS, in any 0.36 mm$^2$, preferably 0.25 mm$^2$, preferably 0.16 mm$^2$, preferably 0.09 mm$^2$, preferably 0.04 mm$^2$, preferably 0.01 mm$^2$, of the analysis surface(s) formed on any one doped conducting layer does not vary from the concentration of dopant atoms in any other 0.36 mm$^2$, preferably 0.25 mm$^2$, preferably 0.16 mm$^2$, preferably 0.09 mm$^2$, preferably 0.04 mm$^2$, preferably 0.01 mm$^2$, of the analysis surface(s) formed on the same conducting layer and which are electrically connected together by more than about 50%, preferably 30%, preferably 20%, preferably 10%. Preferably an individual measurement of the dopant concentration, measured for example by SIMS, is made over an area of greater than 0.01 mm$^2$, preferably greater than 0.04 mm$^2$, preferably greater than 0.09 mm$^2$, preferably greater than 0.16 mm$^2$, preferably greater than 0.25 mm$^2$, preferably greater than 0.36 mm$^2$. This allows for the possibility that there may be local variation of the dopant concentration at some growth sectors, particularly within polycrystalline material such as polycrystalline CVD diamond More preferably, all the analysis surfaces within the device have a uniform dopant concentration, such that the concentration of dopant atoms, as measured for example by SIMS, in any 0.36 mm$^2$, preferably 0.25 mm$^2$, preferably 0.16 mm$^2$, preferably 0.09 mm$^2$, preferably 0.04 mm$^2$, preferably 0.01 mm$^2$ of the analysis surface(s) does not vary from the concentration of dopant atoms in any other 0.36 mm$^2$, preferably 0.25 mm$^2$, preferably 0.16 mm 2, preferably 0.09 mm$^2$, preferably 0.04 mm$^2$, preferably 0.01 mm$^2$ of the analysis surface (s) by more than about 50%, preferably 30%, preferably 20%, preferably 10%. Preferably an individual measurement of the dopant concentration, measured for example by SIMS, is made over an area of less than or equal to 0.36 mm$^2$, preferably less than or equal to 0.25 mm$^2$, preferably less than or equal to 0.16 mm$^2$, preferably less than or equal to 0.09 mm$^2$, preferably less than or equal to 0.04 mm$^2$, preferably less than or equal to 0.01 mm$^2$. This allows for the possibility that there may be local variation of the dopant concentration at some growth sectors, particularly within polycrystalline material such as polycrystalline CVD diamond The simplest way of providing analysis surfaces within a single layer with a uniform dopant concentration across the surface is to provide doped conducting layers with a uniform dopant concentration in the volume of the conducting layer again allowing for the possibility that there may be local variations at some growth sectors. More specifically, it is preferred that the uniformity of dopant within a conducting layer is such that the concentration of dopant atoms, as measured, for example by SIMS in any 1 mm$^3$, preferably 0.2 mm$^3$, preferably 0.03 mm$^3$, volume does not vary from the concentration of dopant atoms in any other 1 mm$^3$, preferably 0.2 mm$^3$, preferably 0.03 mm$^3$ by more than about 50%, preferably 30%, preferably 20%, preferably 10%.

Where the dopant is uniform throughout the volume of the doped conducting layer then any surface formed on the doped conducting layer has a uniform dopant concentration, such that the concentration of dopant atoms, as measured for example by SIMS, in any 0.36 mm$^2$, preferably 0.25 mm$^2$, preferably 0.16 mm$^2$, preferably 0.09 mm$^2$, preferably 0.04 mm$^2$, preferably 0.01 mm$^2$ of the surface on the conducting layer does not vary from the concentration of dopant atoms in any other 0.36 mm$^2$, preferably 0.25 mm$^2$, preferably 0.16 mm$^2$, preferably 0.09 mm$^2$, preferably 0.04 mm$^2$, preferably 0.01 mm$^2$ of the surface of the conducting layer by more than about 50%, preferably 30%, preferably 20%, preferably 10%. Preferably an individual measurement of the dopant concentration, measured for example by SIMS, is made over an area of less than or equal to 0.36 mm$^2$, preferably less than or equal to 0.25 mm$^2$, preferably less than or equal to 0.16 mm$^2$, preferably less than or equal to 0.09 mm$^2$, preferably less than or equal to 0.04 mm$^2$, preferably less than or equal to 0.1 mm$^2$. This allows for the possibility that there may be local variation of the dopant concentration at some growth sectors, particularly within polycrystalline material such as polycrystalline CVD diamond.

The concentration of dopant in different conductive layers may deliberately differ, for example if they are used for different functions, however preferably they have similar concentrations of dopant and thus each of the methods of characterising uniformity of the dopant above apply equally when applied to all conducting layers in the device.

It is well known in the art that the uptake of impurities or dopant element into a growing crystal such as CVD diamond can be sensitive to a number of factors. In particular, the uptake of dopant may be affected by the presence of other defects, such as dislocations or other impurities. In addition, the crystallographic face on which growth is taking place may also affect uptake of dopant. The common crystallographic faces in CVD diamond are the {100}, {110}, {111}, and {113} faces. The relative uptake of impurities in the growth sectors formed by these different faces is very different, and may also vary with growth conditions. For example, the {111} growth sector typically takes up somewhere between 10 and 30 times as much boron as the {100} growth sector. As a consequence of the differential uptake of boron between the different growth sectors, any CVD diamond which includes both the {111} and the {100} growth sectors, such as typical polycrystalline CVD diamond, shows huge local variations in boron concentration. It is for this reason that a maximum sample area or maximum sample volume is generally specified for measurement of uniformity, these areas or volumes being sufficiently small to determine deleterious variation on a larger scale, for example from poor control of the synthesis conditions In embodiments where the diamond of the one or more conductive layers or regions is polycrystalline boron doped diamond, it is preferred that the typical grain size (that is the modal grain size) of the diamond is preferably less than 0.5 times the diameter of the one or more analysis passages, preferably less than 0.3 times the diameter of the one or more analysis passages, preferably less than 0.1 times the diameter of the one or more analysis passages, preferably less than 0.05 times the diameter of the one or more analysis passages.

In embodiments where the conductive layer comprises boron doped single crystal diamond, it is preferred that all the analysis passages traverse a single growth sector.

When the conductive regions comprise boron doped diamond, the resistivity of the boron doped diamond is preferably less than about 10 mΩm (milliohm meters), preferably less than about 5 mΩm, preferably less than about 2 mΩm.

When the conductive regions comprise boron doped diamond, the resistivity of the boron doped diamond is preferably greater than about 0.01 mΩm, preferably greater than about 0.05 mΩm, preferably greater than about 0.1 mΩm, preferably greater than about 0.2 mΩm, preferably greater than about 0.3 mΩm.

The resistivity of a region of boron doped diamond can be calculated by measuring the surface resistance and converting the value obtained to a bulk resistivity measurement.

For instance, when using a four point probe, the surface resistance may be measured by contacting two electrodes with the surface(s) in question at two points separated by a specified distance. A voltage is then applied between the two electrodes. The voltage required to drive a fixed current is measured which allows determination of the surface resistance using Ohm's law, specifically:

$$R=V/I$$

where V is the voltage difference between the two measurement points and I is the forced current flowing between the two measurement points.

An example of a suitable apparatus for determining this measurement is a Jandel Cylindrical hand held Four point Probe in combination with a suitable meter such as a TTi BS407 Precision Milli/Micro Ohm meter.

The surface resistance measured can be used to calculate the electrical resistivity, ρ, of the bipolar electrode using the relationship:

$$\rho = R\pi t/\ln 2$$

where t is the thickness of the region of boron doped diamond in μm and R is the resistance determined as defined above in mΩ.

In general, the resistivity values are not corrected for either the spacing of the measurement points being similar to the thickness of the bipolar electrode nor for the fact that some of the measurements are being made close to the edge of the sample where the theory assumes a semi infinite plane.

Since the microelectrode of the invention is preferably and predominantly composed of diamond, it fundamentally has very high resistance to a wide range of chemicals, very high strength, very high resistance to erosion, very high resistance to abrasion and good stability to temperatures of greater than 500° C. It can therefore be used in aggressive environments such as fluids containing suspended abrasive particles or aggressive chemical species.

The device is capable of being (adapted to be) operated with a fluid flow velocity through the one or more analysis passages of preferably greater than 10 ms$^{-1}$, preferably greater than 20 ms$^{-1}$, preferably greater than 50 ms$^{-1}$, preferably greater than 100 ms$^{-1}$, preferably greater than 200 ms$^{-1}$, preferably greater than 300 ms$^{-1}$.

The device is capable of being (adapted to be) operated with a fluid flow velocity through the one or more intersecting passages of preferably greater than 10 ms$^{-1}$, preferably greater than 20 ms$^{-1}$, preferably greater than 50 ms$^{-1}$, preferably greater than 100 ms$^{-1}$, preferably greater than 200 ms$^{-1}$, preferably greater than 300 ms$^{-1}$.

The device is capable of being (adapted to be) operated with a differential pressure between the front and back surfaces of preferably greater than about 0.05 MPa, preferably greater than about 0.1 MPa, preferably greater than about 0.2 MPa, preferably greater than about 0.5 MPa, preferably greater than about 1 MPa, preferably greater than about 2 MPa, preferably greater than about 5 MPa, preferably greater than about 10 MPa.

When the conductive regions are layers they would normally be of equal thickness and evenly spaced through the body of the microelectrode, although this does not exclude the possibility of the conductive layers being of unequal thickness or unevenly spaced, or both.

The area(s) of electrically conductive diamond in the analysis surface(s) act as the electrochemical electrode surface(s) and come into contact with the fluid under analysis. The fluid is generally a liquid, but may also be a gas.

DETAILED DESCRIPTION OF PREFERRED EMBODIMENTS

As diamond, in particular CVD diamond (conductive and non-conductive), is the preferred material for producing the microelectrode structure of the invention, the invention will be described with particular reference to diamond for convenience. It is to be understood, however, that other appropriate materials are also envisaged. Examples of other appropriate materials for the conductive layer include a metal, an electrically conductive polymer or an electrically conductive ceramic, and examples of other appropriate materials for the essentially non-conducting layers include electrically insulating polymers or ceramics. It would also be possible to combine a conductive diamond layer with non-conductive ceramic materials to form the microelectrode of the invention.

The various components of the preferred diamond microelectrode structure may be single crystal or polycrystalline in nature and will usually be synthetic, although it is possible to fabricate the device at least partially from natural diamond. Synthetic diamond includes high pressure high temperature (HPHT) diamond or chemical vapour deposition (CVD) diamond. The preferred microelectrode structure comprises at least three diamond layers, two that are non-conducting, and an intermediate layer that is conductive. The at least two non-conducting diamond layers are preferably formed of intrinsic diamond.

Whilst CVD diamond is the preferred material for making this invention, it may be appropriate to use a combination of diamond type for the devices. By way of example, an HPHT synthetic diamond can be used to provide mechanical strength in combination with a layer structure fabricated from CVD diamond.

The conductive diamond layer can be fabricated by any chemical vapour deposition method known to the art, but is preferably fabricated by doping during growth, and more preferably by doping with boron during growth. An alternative method of creating the conductive diamond regions is that of ion implantation. Alternative dopants include sulphur and phosphorus.

The various diamond layers are typically, individually, between 5 and 1000 µm in thickness, preferably between 15 and 500 µm in thickness, more preferably between 25 and 300 µm in thickness and most preferably between 50 and 200 µm in thickness.

In order to facilitate the fabrication of the microelectrode of the invention, in particular processing the growth surfaces after synthesis, the thickness of the non-conductive layers in the final microelectrode is preferably greater than 50 µm, preferably greater than 100 µm, preferably greater than 200 µm, preferably greater than 300 µm.

In order to facilitate the fabrication of the microelectrode of the invention, in particular processing the growth surfaces after synthesis, the thickness of the one or more conductive layers in the final microelectrode is preferably greater than 50 µm, preferably greater than 80 µm, preferably greater than 100 µm.

It is preferred that the layers that comprise the microelectrode of the invention are of approximately uniform thickness. In this context uniform means that the thickness of any point of a layer is within the range 70% to 130%, preferably 80% to 120%, preferably 90% to 110%, of the arithmetical average thickness determined by making preferably at least 10 measurements, preferably at least 15 measurements, spread over the area of the layer.

It is preferred that the surfaces upon which successive layers of the microelectrode of the invention are grown have been surface processed such that their surface roughness $R_a$ is less than 1 µm, preferably less than 0.5 µm, preferably less than 0.2 µm, preferably less than 0.1 µm.

The total thickness of the stack of layers that make up the microelectrode is typically between 50 and 3000 µm, preferably between 80 and 1000 µm, more preferably between 100 and 800 µm, and most preferably between 150 and 500 µm. Particularly in applications using very high pressures to provide flow, the microelectrode may be supported by a thicker diamond substrate or non-diamond backing layer.

The lateral shape and extent of the microelectrode is limited only by the technology available for its fabrication. The lateral shape could be circular, square, rectangular, elliptical, or any other shape that is suitable for the application. The lower limit for the lateral extent of the device is defined by the ability to fabricate and mount the device and would typically be about 1 mm, although this does not exclude the possibility of smaller microelectrodes. A large microelectrode could be circular and 100 mm in diameter, although this does not exclude the possibility of larger microelectrodes.

In a further embodiment, the conductive layer or layers could be segmented so that they present a plurality of individually addressable microelectrodes or microelectrode arrays, with each individually addressable area containing one or more passages in which analysis surfaces are formed. This can be accomplished by electrically isolating regions of the electrically conductive diamond layer from each other during the fabrication of the device. One method by which this could be done is by making trenches, for example by laser-cutting, through the electrically conductive diamond layer and just into the underlying intrinsic diamond layer, after it has been deposited and then filling those trenches with intrinsic diamond material during the deposition of the subsequent of intrinsic diamond layer. Analysis passages between the upper and lower major surfaces through the electrically conductive regions are formed. There may be one or more analysis passage per electrically isolated region. The one or more analysis passages in each electrically isolated region may be addressed by making appropriate contacts on to the exposed surfaces of device. In the case of regions of electrically conductive diamond being separated by subsequently filled trenches, the trenches are typically between about 1 µm and about 5 mm wide, preferably between about 50 µm and about 1 mm wide, preferably between about 100 µm and about 500 µm wide. Whilst the trenches ideally have vertical sides and a horizontal base, other cross-section profiles, for example 'V' or 'U' or a flat-bottomed 'V' or any other conceivable cross section profile may be used provided that it provides adequate electrical isolation between adjacent regions.

The individually addressable regions of boron doped diamond should be electrically isolated from each other to avoid "cross talk" between electrical signals. The electrical resistance between any two isolated regions at a temperature of about 300 K is preferably greater than about $1\times10^5$ Ω, preferably greater than about $3\times10^5$ Ω, preferably greater than about $1\times10^6$ Ω. Methods of measuring electrical resistance are well known in the art. One suitable method might be to use an ohm-meter and a pair of contact probes.

In the fabrication of the microelectrode structure one or more analysis passages is/are formed from an exposed major surface of one of the intrinsic diamond layers, through one or more conducting diamond layers, to an exposed major surface of another intrinsic diamond layer, defining respectively one or more inlets and outlets for a fluid, typically a liquid, to flow through the device. The shape of the cross section of the analysis passage is preferably circular, although this does not exclude other shapes such as square or rectangular or any other shape.

The passages are fabricated transverse to the plane of the conductive layer. Whilst it is preferred that the passages are normal to the plane of the conductive layer, there are circumstances when non-normal passages are required, such as when the device is used for in-situ mixing.

The diameter, shape, taper and internal surface roughness of the passages all influence the performance of the microelectrode of the invention.

The surface roughness $R_a$ of the internal surfaces of the passages is preferably less than 2 μm, preferably less than 1 μm, preferably less than 0.5 μm, preferably less than 0.2 μm. In particular, the surface roughness $R_a$ of the internal surfaces of the analysis passages is preferably less than 2 μm, preferably less than 1 μm, preferably less than 0.5 μm, preferably less than 0.2 μm The preferred method of ensuring that the internal surfaces of the passages are sufficiently smooth is laser trepanning where operating parameters such as the traverse rate and the pulse rate are chosen to give required surface finish.

Alternatively, the internal surface of a passage could be processed after being made by laser, for example by techniques using in the fabrication of diamond wire drawing dies, such as polishing the internal surface with a reciprocating wire having a diameter slightly smaller than the passage diameter in a slurry of fine diamond powder.

The lower limit for the diameter of the passages, and in particular the analysis passages, is defined by the technique used for their fabrication. In the case of diamond the preferred technique is to use a yttrium-aluminium-garnet (YAG) laser at a wavelength of approximately 1 μm. With such a laser, the minimum theoretical size of passage would be that produced by a diffraction-limited spot i.e. approximately equal to the wavelength. However, the practical lower limit is about 5 μm. The upper limit of the passage diameter is limited by the lateral dimension of the microelectrode, although a practical upper limit is about 10 mm. The diameter of respective passages is preferably between 15 μm and 2.0 mm, more preferably between 25 μm and 1.0 mm, even more preferably between 35 μm and 0.8 mm and most preferably between 50 μm and 0.5 mm.

A further embodiment uses a KrF excimer laser producing ultraviolet radiation with a wavelength of about 193 nm to fabricate the passages. The shorter wavelength compared with YAG lasers allows the passages to be of smaller diameter, possibly as low as 0.5 μm.

Whilst the use of a YAG laser for fabricating the passages is preferred, this does not exclude the use of alternative techniques such as wavelength tripled 355 nm solid state lasers, other solid state lasers, dye-lasers or other laser systems. A further alternative is the use of electron beams, which are known in the art to be capable of producing very fine holes in diamond.

Whilst the use of a YAG laser for fabricating the trenches is preferred, this does not exclude the use of alternative techniques such as wavelength tripled 355 nm solid state lasers, other solid state lasers, dye-lasers or other laser systems. A further alternative is the use of electron beams, which are known in the art to be capable of producing very fine features in diamond.

The lateral separation of the passages, and in particular the analysis passages, is determined by the nature of the process the MEA is required to monitor. From a fabrication viewpoint, the centre-to-centre separation of the passages is preferably at least one-and-a-half-times the diameter of the passages or else the device may be too fragile. More preferably, the separation is at least twice the passage diameter and most preferably it is at least three times the passage diameter. Larger separations might be required in embodiments where each passage can be separately electrically addressed.

There are no absolute requirements on the disposition of the passages, and in particular the analysis passages, on the lateral surface provided they meet the spacing requirements previously referred to. However, it is preferred that the passages, and in particular the analysis passages, are arranged in a regular array, such as a triangular array, a square array or a hexagonal array, to facilitate easier fabrication.

The electrical contacts can be made either to the outer edges of the microelectrode array or to specially prepared regions which are preferably coplanar with the major surfaces of the device. Both configurations of electrical contacts are compatible with all the embodiments described within this specification.

The electrical contacts to the boron doped regions of the device are essential for obtaining good performance. Preferably the contacts should be ohmic and have a contact resistance of preferably less than $1\times10^{-5}$ Ω per $cm^2$, preferably less than $3\times10^{-6}$ Ω per $cm^2$, preferably less than $1\times10^{-6}$ Ω per $cm^2$. The region where the contact is to be deposited can be prepared by laser milling the surface. Methods of preparing low contact resistance ohmic contacts on boron doped diamond are known in the art. An example of a contact material that provides the preferred level of contact resistance is a titanium-gold contact (where the Ti layer is adjacent to the diamond). Other examples might include titanium-platinum-gold, chromium gold (where the titanium or chromium layer is in contact with the boron doped diamond. As is well known in the art, the performance of electrodes can be improved by annealing for a few minutes at a moderate temperature (typically about 300-500° C.), thereby forming a carbide interlayer between the diamond and the adjacent metal layer. Connection to these contact regions can be made mechanical means e.g. a pressure contact, wire bonding, by soldering, or by other methods known in the art.

The reference electrode against which the potential of the microelectrode of the invention is measured can be a standalone electrode (that is physically separate from the microelectrode of the invention) or an in-situ device (for example fabricated on a surface of the microelectrode of the invention). An example of a reference electrode is a Ag/AgCl electrode, the use of which is widely known in the art.

BRIEF DESCRIPTION OF THE DRAWINGS

FIGS. 8A and 8B are schematic diagrams of the microelectrode array of Example 4 in which an annular contact area is provided.

Particular embodiments of the invention will now be described with reference to the accompanying drawings. Referring to FIG. 1, a microelectrode 10 comprises three layers 12, 14 and 16 of non-conducting diamond intimately attached during CVD synthesis to two layers 18 and 20 of conducting diamond in a stacked arrangement. The device includes a plurality of analysis passages 22, arranged in an array, extending through the conducting and non-conducting diamond layers 12 to 20, as shown more clearly in FIG. 2. The passages 22 define respective inlets 24 and outlets 26, and provide areas 28 of conducting diamond in the passage surfaces 30. These surfaces are referred to as the "analysis surfaces". The respective outer surfaces 32 and 34 of the layers of conducting diamond 18 and 20 provide locations at which connections to the external monitoring circuits can be made. Steps or other processing at the edges of the device may assist in making these connections.

In order to analyse a liquid or other fluid, the fluid is flowed or pumped through the analysis passages 22 where it is exposed to the conducting areas 28. An electrical signal from the microelectrode is passed via an external electrical circuit (not shown) to instrumentation that can convert it to a signal associated with a characteristic being monitored.

Figure 1:
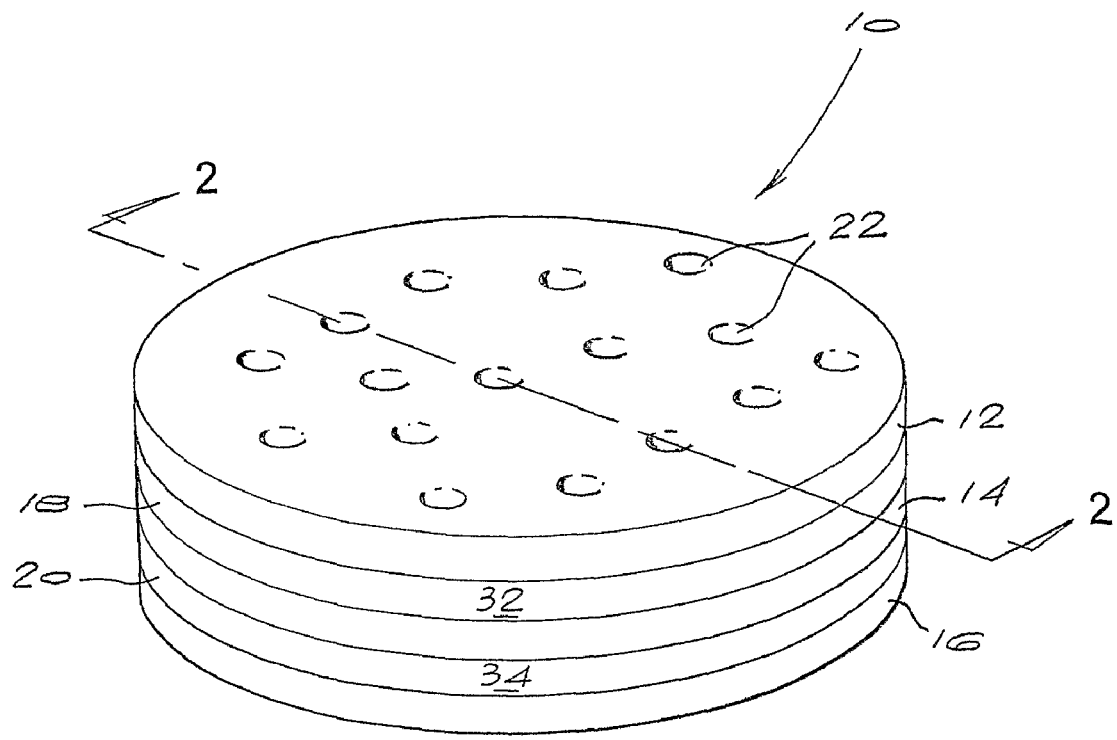
FIG. 1 is a perspective view of a first preferred embodiment of a microelectrode of the invention.
Figure 2:
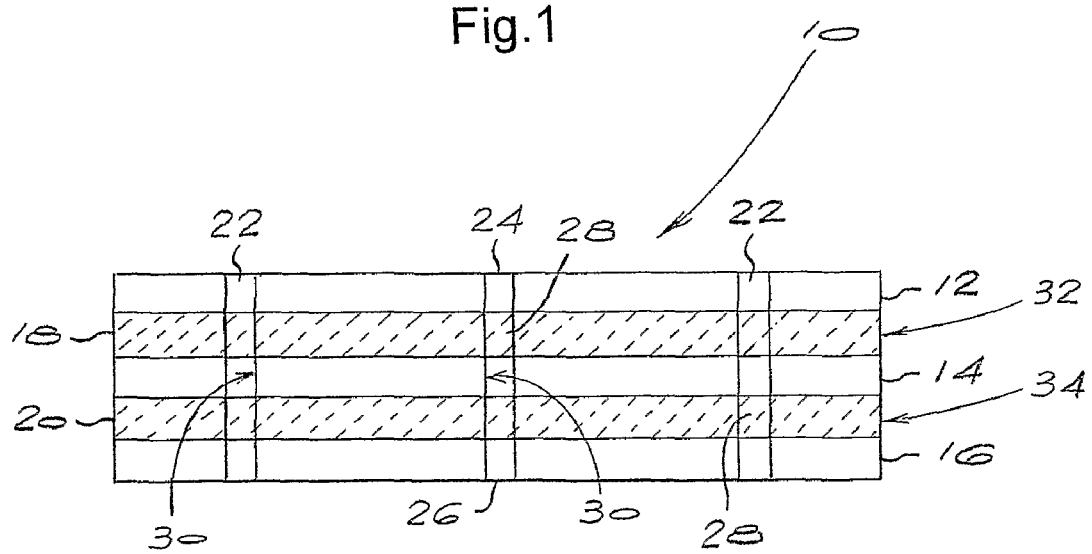
FIG. 2 is a sectional side view of the microelectrode of FIG. 1 on the line 2-2.
Figure 3:
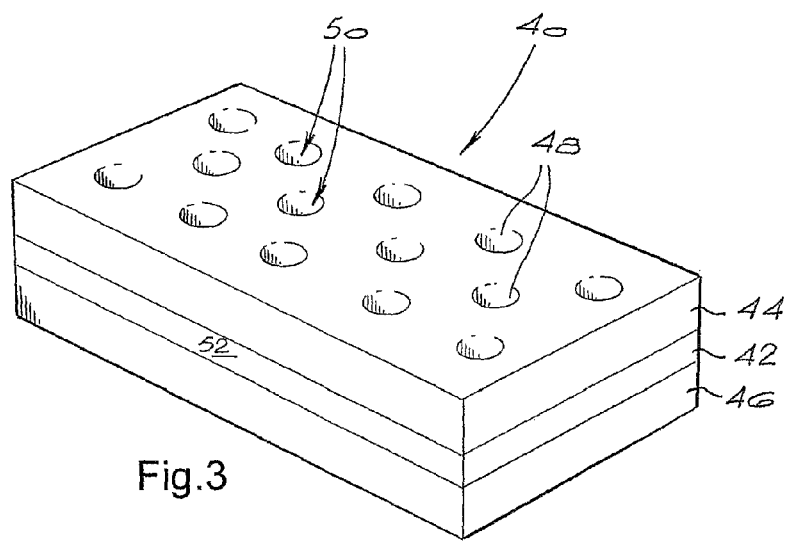
FIG. 3 is a perspective view of a second preferred embodiment of a microelectrode of the invention.

The embodiment of FIGS. 1 and 2 is circular in plan view. However, as has already been mentioned, any appropriate shape can be used. Accordingly, referring to FIG. 3, there is shown an alternative embodiment of the invention in which the microelectrode 40 is rectangular in plan view. It consists of a layer 42 of conducting diamond sandwiched between two layers 44 and 46 of non-conducting diamond, and includes a plurality of analysis passages 48, arranged in an array, extending through the conducting and non-conducting diamond layers. The passages 48 define respective inlets 50 and outlets (not shown), and provide area of conducting diamond (also not shown) similar to those described with reference to FIGS. 1 and 2. The outer surface 52 of the conducting diamond layer 42 provides a location at which connections to the external monitoring circuits can be made.

Analysis of a liquid or other fluid is carried out in a manner substantially as described above.

Figure 4:
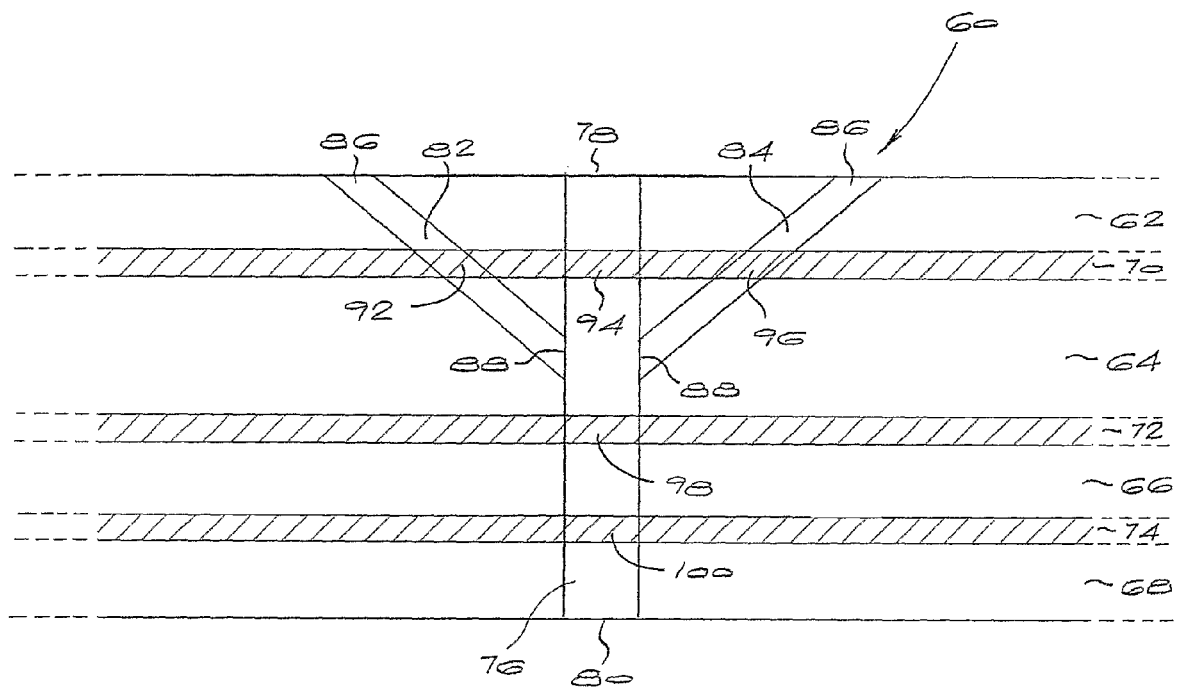
FIG. 4 is a cross-sectional side view of a portion of a third preferred embodiment of a microelectrode of the invention.

In both of the embodiments described above, the passages (22, 48) extend normal to the plane of the conducting diamond layers (18/20, 42). However, some or all of the passages could be fabricated at an angle, and may even intersect, as shown in the embodiment of FIG. 4. Referring to FIG. 4, the microelectrode 60 consists of layers 62, 64, 66 and 68 of non-conducting diamond bonded to respective layers 70, 72 and 74 of conducting diamond in a stacked arrangement. An analysis passage 76 (only one is shown for convenience) extends through the conducting and non-conducting diamond layers and defines an inlet 78 and an outlet 80. Two further intersecting passages 82 and 84 extend transversely through the layers 62, 70 and 64 and intersect the passages 76. The passages 82 and 84 define respective inlets 86 adjacent inlet 78 and outlets 88 in the passage 76. This arrangement allows for the introduction of different reactants via inlets 78 and 86 and for mixing in the passage. In so doing, the individual reactants can be analysed through contact with the respective analysis surfaces 90, 92 and 94, whilst the reaction product can be analysed through contact with the respective analysis surfaces 98 and 100.

Where there are only one or two conductive layers, an alternative method of connecting the conductive layer(s) to an external circuit would be to make one or more 'blind' holes in from one or both of the large planar surfaces of non-conducting diamond, such that the blind holes extend as far as (or just beyond) its adjacent conducting layer. The holes could be filled with a conductive material, such as a metal or metal loaded polymer (e.g. silver loaded epoxy resin), and connection to the external surface made from this location. It would be necessary to encapsulate the location(s) on the external surface at which this connection was made to ensure that no current leakage could occur.

Once provision has been made to facilitate connection to an external circuit, the outer surface of the device is encapsulated in a suitable polymeric material, for example a silicone or an epoxy resin, to prevent cross talk between signals from different layers.

It is envisaged that the device would be incorporated in the bore of a tube or the wall of a reaction vessel such that fluid could flow or be forced through the analysis passages. A separate feed may be provided for the fluid entering through the intersecting passages.

Alternatively, in the embodiment where the device is used to monitor reactions occurring in-situ in the electrode, the multiple inlet passages would be individually supplied with reactants via, for example, capillary tubes.

Figure 5:
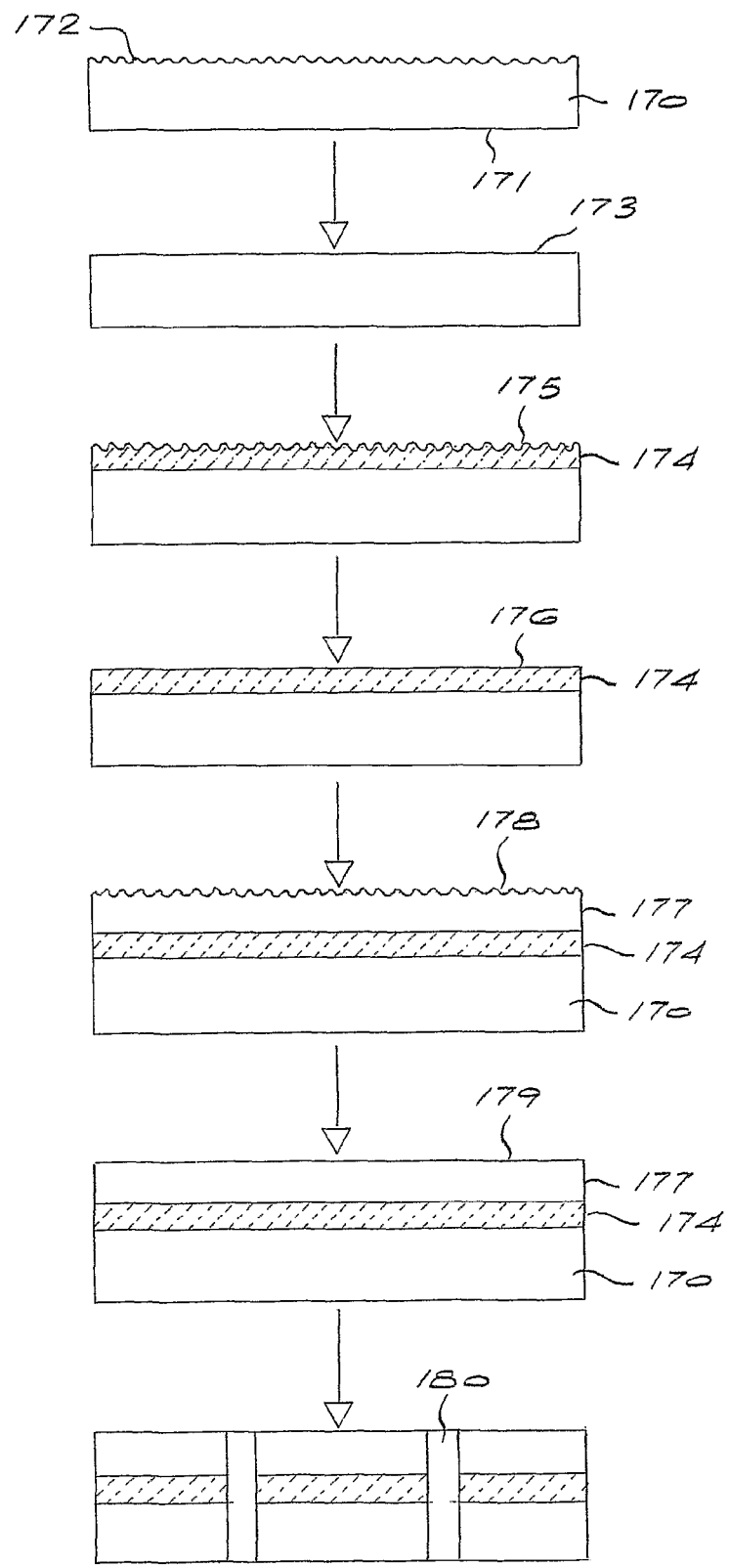
FIG. 5 is a schematic diagram illustrating a typical manufacturing route for a microelectrode of the invention.

FIG. 5 illustrates a general manufacturing route for preparing a microelectrode according to the present invention and described in more detail in Example 1. In FIG. 5 a first intrinsic diamond layer 170 is provided including a nucleation surface (as-grown) 171 and a growth surface 172. The growth surface 172 is subsequently lapped to provide a lapped growth surface 173 onto which a boron doped layer 174 is grown. The boron doped layer 174 includes an as-grown surface 175 which is subsequently lapped to provide a lapped surface 176.

A second intrinsic diamond layer 177 is grown on the lapped surface 176 of the boron doped layer 174. The second intrinsic diamond layer 177 includes an as-grown surface 178 which is subsequently lapped to provide a lapped surface 179.

Laser drilled holes 180 are drilled through the second intrinsic diamond layer 177, the boron doped layer 174 and the first intrinsic diamond layer 170.

Figure 6:
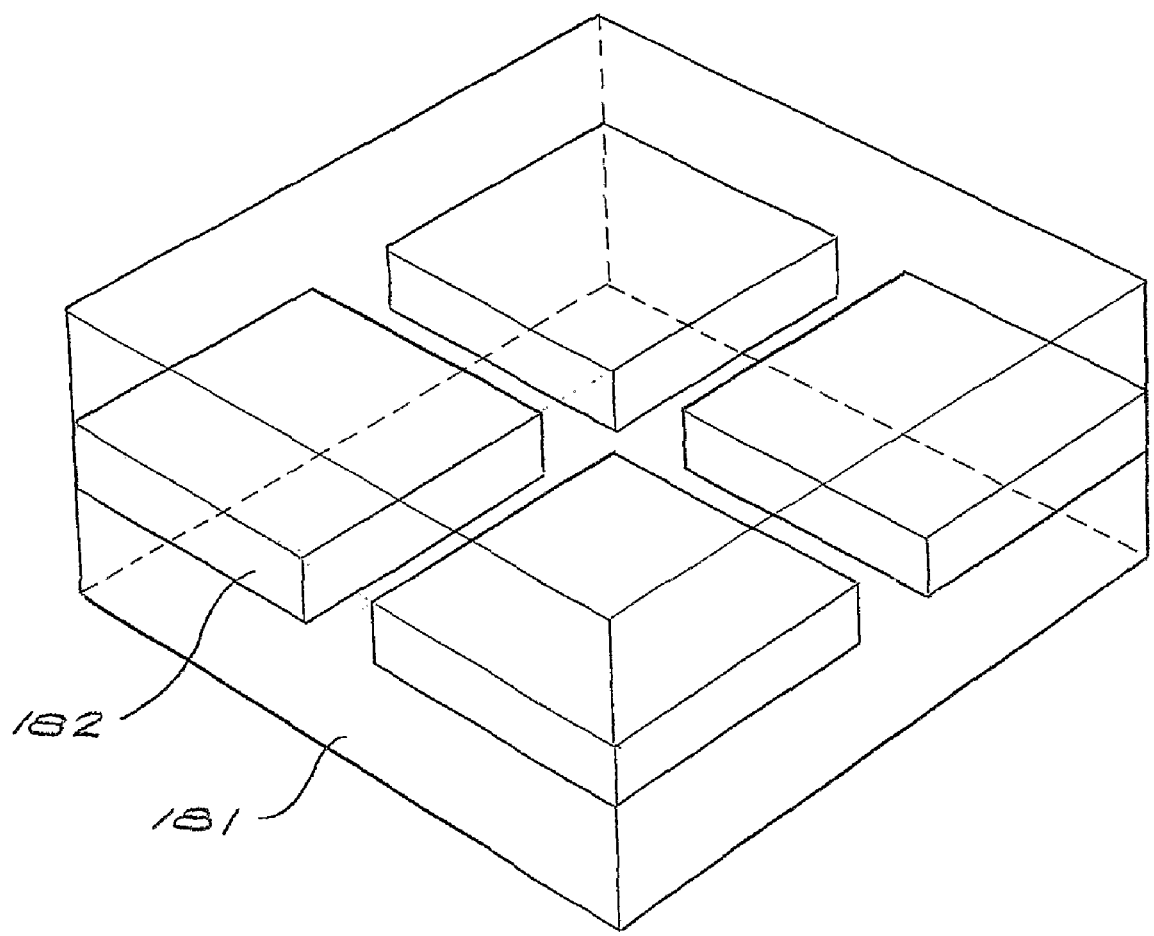
FIG. 6 a perspective view of a fourth preferred embodiment of a microelectrode of the invention.

FIG. 6 shows a segmented, addressable microelectrode detector according to one aspect of the present invention which includes a 'block' of intrinsic diamond 181 including boron doped diamond pads 182. Channels (not shown) are drilled down through the intrinsic diamond 181 and the boron doped pads 182.

Figure 7:
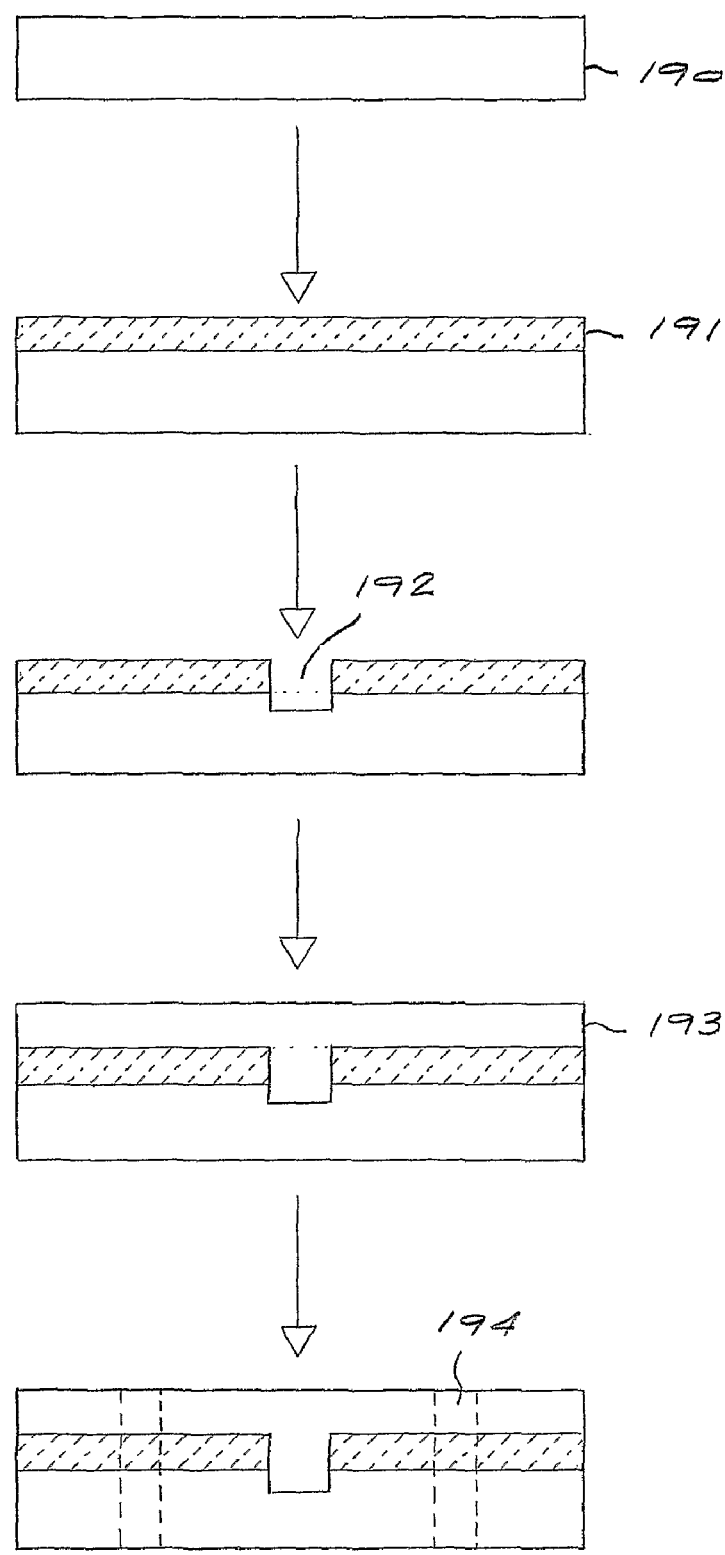
FIG. 7 is a schematic diagram of a manufacturing route for a microelectrode of the fourth embodiment of the invention illustrated in FIG. 6.

FIG. 7 illustrates a general manufacturing route for preparing a segmented addressable microelectrode detector according to the present invention. In FIG. 7 a first intrinsic diamond layer 190 is provided onto which a boron doped diamond layer 191 is grown. A trench 192 is cut through the boron doped diamond layer 191 and a second intrinsic diamond layer 193 grown over the boron doped layer 191 and trench 192. Subsequently a laser drilled channel 194 is drilled through the second intrinsic diamond layer 193, boron doped diamond layer 191 and first intrinsic diamond layer 190.

FIGS. 8A and 8B illustrate a microelectrode further described in Example 4 (below). FIG. 8A is a plan view and FIG. 8B a cross section view through A-A in FIG. 8A. A circular plate with a nominal diameter (a) of 6 mm was prepared as in Example 1. The thicknesses of the layers were as follows:

first intrinsic diamond layer 101—about 500 µm thick,
boron doped diamond layer 103—about 100 µm thick, and
second intrinsic layer 102—about 150 µm thick.

An annulus of material 0.5 mm in width was laser milled away from the second intrinsic layer 102 and from part of the boron doped diamond layer 103, exposing an annulus of boron doped diamond 103 and 5.0 mm diameter (b) plateau of second intrinsic layer. The exposed annular region is subsequently used for making the contact to the microelectrode array (not shown). The depth of the surface of the annulus below the remainder of the surface of the second intrinsic layer (c) was nominally 0.20 mm.

A square array of nine analysis passages 104 (a 3×3 array centred on the centre of the microelectrode) was laser drilled from the exposed surface of the second intrinsic layer 102. The passages were nominally 0.20 mm in diameter (d) with a nominal centre-to-centre separation of 0.80 mm (e).

Types of electrical signal from the microelectrode array of the invention that could be measured include:

faradic, that is voltages or potential differences associated with redox electrochemistry;
conductometric, that is associated with the number or concentration of ions in a solution; and
coulometric, that is associated with the amount of charge passed.

The electrical measurement from the microelectrode array of the invention could be conducted by a wide range of techniques including:

continuous flow, where the analyte is in the solution at all times;
flow injection analysis ("FIA"), where a small volume of the analyte is injected into the flow stream;
application of a potential and measuring a current, optionally using pulsing techniques to increase the sensitivity;
indirect electrochemical detection of species where an electrochemically inactive species reacts to form an electrochemically active species that can be detected; and
stopped flow techniques for "exhaustive" electrochemistry.

All of the above techniques can be combined with spectroscopic measurements by using the intrinsic diamond layer or layers as an optical window.

The microelectrodes of the invention may be used in a wide variety of applications such as:

the measurement of trace heavy metals such as lead, cadmium, copper and zinc in the environment (e.g. Sono-Cathodic Stripping Voltammetry of Lead at a Polished Boron-Doped Diamond Electrode: Application to the Determination of Lead in River Sediment, Saterlay et al, Electroanalysis 1999, 11, No. 15, p 1083;
the detection of organic or bio-chemical compounds such as carboxylic acids in enology, food processing and wastewater analysis applications (see Chailapakul et al, Electrochem. Commun., 2000, Volume 2, p 422) or DNA in flow detection systems (Rao et al, New Diamond and Frontier Technology, vol. 13, No 2, 2003, p 79); and
the detection of biomolecules such as thyroid hormones (Yvonne Naidoo, Electrochemical Behaviour of Boron Doped Diamond Electrodes, MSc Thesis, University of Pretoria, 2001).

The microelectrode could also be used for many other kinds of chemical and physical-chemical measurements, including:

chemical analysis by measurement of electrode potentials;
monitoring chemical reactions or electrochemical processes that occur on very short time scales;
optimised design for mixing/reactions and structured flow geometry (e.g. structured flow channel diameter enabling measurements at different flow speeds in the same diamond device);
multi-electrode structures for time-of-flight measurement of different species, enabling lifetime and kinetic information to be extracted;
electrochemical generation/collection experiments;
hydrodynamic modulation voltammetry for low concentration detection (e.g. sub-micro-molar) of electroactive species (pulsed flow and/or pulsed potential enables lock in detection to be utilised);
using the presence of multiple sensitive areas in a single analysis passage or array of analysis passages to 'time slice' chemical reactions and thereby monitor their progress as a function of time and on very short time scales;
probing reactions with lasers or other optical probes to allow in-situ spectroscopic measurements of reactions;
probing with lasers through the non-conductive parts of the electrode to allow localised heating of the fluid, or even, through the use of wavelengths that are only absorbed by one chemical species, for heating a single chemical species within the fluid (the high thermal conductivity of the diamond could be subsequently utilised to enable rapid cooling once outside the heating zone; indeed local temperature control could be included, as the high thermal conductivity could be used to keep the fluid cool);
some boron doped layers could be designed to be resistive heaters allowing reactions to be studied as a function of temperature;
probing with laser or other light to perform in-situ photo-electrochemistry (all techniques which combine photo-chemical and electrochemical methods for the study of the oxidation-reduction chemistry of the ground or excited states of molecules or ions. In general, it is the chemistry resulting from the interaction of light with electrochemical systems. Spectroscopic techniques used to investigate/monitor species in solution could include infrared/ultraviolet/visible absorption spectroscopy, luminescence/fluorescence. Simultaneous optical/electrochemical monitoring/ generation would be possible within the cell);
making in-situ flow measurements using laser Doppler techniques (laser Doppler Anemometry/Laser Doppler Velocimetry to measure the velocity of the seeded particles conveyed by a fluid flow. The seeded particles must be big enough to scatter sufficient light for signal detection (good signal to noise ratio) but small enough to follow the flow (laminar or turbulent) faithfully (in-synchronisation with the localised fluid motion). By analysing the Doppler-equivalent frequency of the laser light scattered (intensity modulations within the crossed-beam probe volume) by the seeded particles within the flow, the local velocity of the fluid can be determined (Yeh, Y. & Cummins, H., 1964, 'Localised fluid flow measurements with a He—Ne laser spectrometer', Appl. Phys. Lett., 4, pp. 176-178));

the extreme properties of diamond could be utilized to enable electrochemical measurements, or any of the above techniques, under extreme conditions of temperature, pressure etc; and using an array in which multiple channels intersect to monitor reactions combined with any of the techniques described above.

The structure of the microelectrode, consisting as it does of alternating non-conducting and conducting (preferably boron doped) diamond layers, also enables it to be used in part as a micro-electro-osmotic pump, in which the applied voltage on certain of the conductive layers is varied with time causing the fluid in the passages to be pumped along the passages. Electro-osmosis refers to the fluid flow that occurs when an electric field is applied to the electrical double layer. This phenomenon is important for microfluidic applications since pressure-driven flows in small channels exhibit a parabolic velocity profile, with an average velocity proportional to the second power of the transverse dimension of the channel. Hence, large pressures are required to pump fluids in small channels. Electro-osmosis produces a "plug-flow profile" and the velocity is approximately independent of channel size. Due to the absence of moving components, microfluidic control and fluid handling devices using electro-osmosis are more reliable and easier to maintain compared with microsystems that have moving surfaces, valves or pistons. Hence the conducting diamond layers could be used (in addition to their role as electrodes for electrochemistry) to activate fluid flow through the device, and also to enable cleaning of the device.

It is also envisaged that rather than using the microelectrode structure to analyse, or solely analyse a fluid, it could also be used to process a fluid, either as part of or as an alternative to the analyses. The fluid may be processed to modify the fluid by means of mixing and/or to modify the fluid by electrical means or by electrochemical means, for example by providing an electrical current between two or more conducting layers, and in some instances measuring the current or voltage present at other conducting layers to, for example, characterise the extent of the chemical reaction being driven. This processing of a fluid may form part of the analysis process, enabling further electrodes downstream to characterise the modified fluid, or enabling further external forms of measurement to be made on the fluid, or it may form an intermediate or final product for use external to the microelectrode structure. Included in the concept of processing the fluid is partially or totally converting a liquid to a gas. Thus, although the term 'analysis passage' is used, the passage can also be used for processing of the fluid, or for combined processing and analysis. In addition, the design of the microelectrode structure, and in particular the exits of the passages and the pressure present at the entrance and exit surfaces of the microelectrode, may be such as to disperse a liquid exiting the structure in the form of liquid droplets or an aerosol suspension in a gas.

It is also envisaged that customised non-diamond electrodes (e.g. metal electrodes) could be integrated into the diamond microelectrode by selective metal deposition on one or more of the boron layer electrodes. The metal band electrodes fabricated in this way could be used as local reference/counter electrodes enabling/enhancing applications involving multiple electrodes under independent control (e.g. generation/collection).

The diamond microelectrode structure of the invention provides improved flexibility over existing MEAs, and in particular offers the following advantages over the prior art:

1. The layers are individually addressable and areas of individual layers may be individually addressed.
2. The analysis passages can be packed much more tightly than the individual electrodes of a conventional array and therefore the output signal can be much higher.
3. The liquid or other fluid being monitored can be pumped or flowed past the electrodes rather than being dependent on diffusional transport mechanisms in essentially stagnant conditions.
4. By biasing the different layers or areas of layers at different voltages, several reactions can be monitored with the same electrode array.
5. Although the structure can be made from other materials, the large solvent window, low background current, the erosion and abrasion resistance and general resistance to chemical attack of diamond make it a particularly attractive material.
6. The erosion and abrasion resistance of diamond is such that fluids that are highly erosive and/or abrasive can be monitored.
7. By using the invention in a configuration where in-situ mixing can occur, it can be used for making electrochemical measurements on reactions on very short timescales.

EXAMPLES

The fabrication and use of the current invention are described by means of the following examples.

Example 1

The route for the fabrication of the diamond microelectrode of the first embodiment of the invention is shown in FIG. 5.

A plate of intrinsic polycrystalline diamond about 500 µm thick and 24 mm in diameter was prepared. The growth surface of the plate was mechanically processed to a surface roughness $R_a$ of less 100 nm by lapping. The nucleation surface was in the as-grown state and had a surface roughness $R_a$ of less than 1 µm. After preparing the surface, the plate was cleaned using a hot oxidising mixture of concentrated sulphuric acid and potassium nitrate at a temperature greater that 150° C.

The plate was placed inside chemical vapour deposition (CVD) system capable of depositing boron-doped diamond. A layer of boron doped diamond about 140 µm thick was deposited onto the growth surface. The deposition conditions were chosen to provide a boron concentration in the deposited layer of between about $2\times10^{20}$ atoms per $cm^3$ (about 1000 ppm) and about $1\times10^{21}$ atoms per $cm^3$ (about 5000 ppm). After deposition of the boron doped layer, the plate was removed from the synthesis system and the growth surface was lapped taking the total thickness of the plate to approximately 600 µm. After lapping the plate was again cleaned. The surface roughness $R_a$ of the lapped plate was less than 100 nm. The plate was placed in a further CVD diamond deposition system and a layer of intrinsic diamond about 250 µm thick was deposited on the growth surface. After removal from the deposition system, the growth surface of the plate was again lapped to a surface roughness $R_a$ of less than 100 nm, and the plate had a total thickness of about 800 µm.

An array of 7 holes with a diameter of 0.6 mm was drilled through the thickness of the plate using a 1.06 µm Nd:YAG laser system. The holes arranged in a hexagonal array with a centre-to-centre separation of 2 mm.

A contact was made to the exposed edge of the boron doped diamond layer. The microelectrode array was packaged using a PTFE (polytetrafluoroethylene, also known as "TEFLON®") tube such that a fluid could be flowed through the array.

Example 2

A plate consisting of an intrinsic diamond layer, a boron doped diamond layer and a further intrinsic layer was prepared as in Example 1. After the lapping and cleaning stage, a further layer of boron doped diamond ("second boron-doped diamond layer") about 140 μm thick was deposited on to one of the surface. After deposition, the surface of the second boron doped diamond layer was lapped to a surface roughness $R_a$ of less than 100 nm and thickness of about 100 μm. After a further cleaning step using the hot oxidising mixture of concentrated sulphuric acid and potassium nitrate at a temperature greater that 150° C., a further intrinsic diamond layer, about 250 μm thick, was deposited on top of the second boron doped diamond layer. This layer was lapped to a surface roughness $R_a$ of less than 100 nm and a thickness of about 200 μm.

The synthesised stack of diamond layers thus comprised:
an intrinsic diamond layer about 500 μm thick,
a boron-doped diamond layer about 100 μm thick ("first boron doped diamond layer"),
an intrinsic diamond layer about 200 μm thick,
a boron-doped diamond layer about 100 μm thick (second boron doped diamond layer), and
an intrinsic diamond layer about 200 μm thick.

Electrical measurements contacting the exposed edges of the first boron doped diamond layer and the second boron doped diamond layer showed that the electrical resistance between them was greater than 1 MΩ, the limit of the meter used.

An array of 7 holes with a diameter of 0.5 mm was drilled through the thickness of the plate using a 1.06 μm Nd:YAG laser system. The holes arranged in a hexagonal array with a centre-to-centre separation of 3 mm.

Contacts were made to the exposed edges of the boron doped diamond layers. The microelectrode array was packaged using a PTFE (polytetrafluoroethylene, also known as "TEFLON®") tube such that a fluid could be flowed through the array.

Example 3

A schematic perspective view of the third embodiment of the diamond microelectrode of the invention is shown in FIG. 6 and a route for its fabrication is shown in FIG. 7.

A plate of intrinsic polycrystalline diamond about 500 μm thick and 24 mm in diameter was prepared. The growth surface of the plate was mechanically processed to a surface roughness $R_a$ of less 100 nm by lapping. The nucleation surface was in the as-grown state and had a surface roughness $R_a$ of less than 1 μm. After preparing the surface, the plate was cleaned using a hot oxidising mixture of concentrated sulphuric acid and potassium nitrate at a temperature greater that 150° C.

The plate was placed inside chemical vapour deposition (CVD) system capable of depositing boron doped diamond. A layer of boron doped diamond about 140 μm thick was deposited onto the growth surface. The deposition conditions were chosen to provide a boron concentration in the deposited layer of between about $2 \times 10^{20}$ atoms per cm$^3$ and about $1 \times 10^{21}$ atoms per cm$^3$. After deposition of the boron doped layer, the plate was removed from the synthesis system and the growth surface was lapped taking the total thickness of the plates to approximately 600 μm. After lapping the plate was again cleaned. The surface roughness $R_a$ of the lapped plate was less than 100 nm.

Two trenches intersecting each other at about 90° were cut through the boron doped diamond layer and just into the underlying intrinsic diamond layer such that the boron doped layer was divided into four approximately equal quadrants. The trenches had a width of approximately 200 μm. After thorough cleaning using the mixture of hot concentrated sulphuric acid and potassium nitrate, the plate was placed in a further CVD diamond deposition system and a layer of intrinsic diamond about 300 μm thick was deposited on the growth surface and filling the isolating trenches; the additional growth thickness is required to ensure that there is sufficient material above the trenches for the growth surface to be processed flat. After removal from the deposition system, the growth surface of the plate was again lapped to a surface roughness $R_a$ of less than 100 nm, and the plate had a total thickness of about 800 μm.

Electrical measurements contacting the exposed edges of the conductive diamond layer showed that the electrical resistance between electrically isolated regions was greater than 1 MΩ, the limit of the meter used.

An array of 4 holes (arranged in a square) with diameters of 0.5 mm and centre-to-centre separation between adjacent holes of 2 mm was drilled through the thickness of the plate in each electrically isolated regions of the microelectrode array using a 1.06 μm Nd:YAG laser system.

A contact was made to the exposed edge of each of the electrically isolated regions of the boron-doped diamond layer. The microelectrode array was packaged using a PTFE (polytetrafluoroethylene, also known as "TEFLON®") tube such that a fluid could be flowed through the array.

Example 4

The microelectrode of Example 4 is described with reference to FIG. 8.

A circular plate with a nominal diameter of 6 mm was prepared as in Example 1. The thicknesses of the layers were as follows:
first intrinsic diamond layer—about 500 μm thick,
boron doped diamond layer—about 100 μm thick, and
second intrinsic layer—about 150 μm thick.

An annulus of material 0.5 mm in width was laser milled away from the second intrinsic layer and from part of the boron doped diamond layer, exposing an annulus of boron doped diamond. This exposed annular region is subsequently used for making the contact to the microelectrode array. The depth of the surface of the annulus below the remainder of the surface of the second intrinsic layer was nominally 0.20 mm.

A square array of nine analysis passages (a 3×3 array centred on the centre of the microelectrode) was laser drilled from the exposed surface of the second intrinsic layer. The passages were nominally 0.20 mm in diameter with a nominal centre-to-centre separation of 0.80 mm.

Contacts were prepared on the previously exposed annulus of boron doped diamond by coating the whole device except for the annulus with resist, depositing a layer of titanium between about 5 nm and about 50 nm thick by sputtering, followed by depositing a layer of gold about 0.5 μm to about 2 μm by sputtering. The contacts were then annealed at a temperature of about 400° C. in a protective nitrogen environment for approximately 5 minutes.

Contact to an external circuit was made using an "oxygen free" copper strip about 0.30 mm thick with a central aperture nominally 5 mm diameter that fitted onto the annular contact area. It is known in the art that low contact resistances can be achieved between copper and gold simply by applying pressure.

The microelectrode array was packaged between a pair of PTFE cylinders with central bores of fractionally over 5.0 mm that were intended to prevent contact of the fluid passing through the microelectrode array coming into contact with the contact to the external measurement circuit.

The PTFE-microelectrode array assembly itself was housed in a two-piece brass assembly that kept the PTFE-microelectrode array assembly in compression and enable it to be incorporated into a pipe or tube.

Micro Ag/AgCl reference electrodes were inserted into the tube upstream and downstream of the microelectrode array.

The invention claimed is:

1. A microelectrode comprising:
a body formed from electrically non-conducting material and including at least one region of electrically conducting material and at least one passage extending through the body of non-conducting material and the region of conducting material, the electrically conducting region presenting an area of electrically conducting material to a fluid flowing through the passage in use,
wherein the electrically conducting material is electrically conducting diamond and the non-conducting material is non-conducting diamond.

2. A microelectrode according to claim 1, wherein the body includes more than one region of electrically conducting material and the passage passes through the body of electrically non-conducting material and through the regions of electrically conducting material.

3. A microelectrode according to claim 1 or claim 2, wherein the region or regions are in the form of a layer or layers.

4. A microelectrode according to claim 1, wherein the body comprises a layered structure comprising at least two spaced layers of non-conducting material and at least one layer of conducting material sandwiched between the layers of non-conducting material and at least one passage formed through the layers in a direction transverse to the layers.

5. A microelectrode according to claim 4, wherein each layer has a thickness in a range of 5 to 1000 microns.

6. A microelectrode according to claim 4, wherein a total thickness of the layered structure is in a range of 50 to 3000 microns.

7. A microelectrode according to claim 1, where the passage is an analysis passage.

8. A microelectrode according to claim 1, wherein the body has a plurality of passages passing through it and through the region or regions of electrically conducting material.

9. A microelectrode according to claim 8, wherein the passages form a regular array.

10. A microelectrode according to claim 9, wherein the passages form an irregular array.

11. A microelectrode according to claim 10, wherein a dopant concentration is uniform through a conductive layer such that a dispersion of dopant when viewed over a whole volume of the electrode is such that the concentration of dopant atoms, as measured by SIMS, in any 1 mm$^3$ volume does not vary from the concentration of dopant atoms in any other 1 mm$^3$ volume by more than about 50%.

12. A microelectrode according to claim 8, wherein all the passages have a circular cross-section.

13. A microelectrode according to claim 12, wherein all the passages have the same diameter.

14. A microelectrode according to claim 12, wherein a diameter of the passages is in a range of 5 microns to 10 mm.

15. A microelectrode according to claim 8, wherein the passages are all separate from one another.

16. A microelectrode according to claim 15, wherein a separation between passages is at least twice a diameter of the passages.

17. A microelectrode according to claim 16, wherein a separation between passages is at least three times a diameter of the passages.

18. A microelectrode according to claim 8, wherein one or more of the passages intersect another passage or passages.

19. A microelectrode according to claim 18, wherein one or more intersection passages intersect one or more analysis passages.

20. A microelectrode according to claim 1, wherein the electrically conducting diamond is boron doped diamond.

21. A microelectrode according to claim 1, wherein the diamond is CVD or HPHT diamond.

22. A microelectrode according to claim 21, wherein a dopant concentration is uniform such that the concentration of dopant atoms on an analysis surface(s) of a conducting layer, as measured by SIMS, in any 0.36 mm$^2$ area of an analysis area, does not vary from the concentration of dopant atoms in any other 0.36 mm$^2$ of an analysis area by more than about 50%.

23. A microelectrode according to claim 21, wherein a dopant concentration is uniform such that the concentration of dopant atoms on any surface of a conducting layer, as measured by SIMS, in any 0.36 mm$^2$ area, does not vary from the concentration of dopant atoms in any other 0.36 mm$^2$ of area by more than about 50%.

24. A microelectrode according to to claim 21, wherein a dopant concentration is uniform across all conductive layers in the device.

25. A microelectrode according to claim 21, wherein, where the conductive region or layer comprises boron doped single crystal diamond, all the passages traverse a single growth sector.

26. A microelectrode array according to claim 25, wherein, where the conductive region comprises boron doped single crystal diamond, all the analysis passages traverse a single growth sector.

27. A microelectrode according to claim 21, wherein, where the diamond of the one or more conductive layers or regions is polycrystalline boron doped diamond, a typical grain size (modal grain size) of the diamond is less than 0.5 times a diameter of the one or more passages.

28. A microelectrode according to claim 1, wherein the region or regions of electrically conducting material are in electrical contact with an external surface of the body.

29. An electrochemical cell which includes a microelectrode according to claim 1.

30. A microelectrode according to claim 1, wherein the device is adapted to be operated with a fluid flow velocity through the one or more passages of greater than 10 ms$^{-1}$.

31. A microelectrode according to claim 1, wherein the device is adapted to be operated with a differential pressure between front and back surfaces of greater than about 0.05 MPa.

32. A microelectrode according to claim 1, wherein the microelectrode is a micro-electro-osmotic pump.

33. A microelectrode according to claim 1, further comprising:
separately addressable layers.

34. A microelectrode according to claim 1, further comprising:
separately addressable regions.

35. A microelectrode according to claim 34, further comprising:
separately addressable regions and separately addressable layers within the same microelectrode.

36. A microelectrode according to claim 1, further comprising:
a reference electrode as an in-situ device.

37. A microelectrode according to claim 36, wherein the reference electrode is fabricated on a surface of the microelectrode.

38. A method comprising:
applying a voltage on certain conductive layers of a microelectrode, the applied voltage being varied with time causing a fluid in passages to be pumped along the passages,
wherein the microelectrodes comprises a body formed from electrically non-conducting material and including at least one region of electrically conducting material and at least one passage extending through the body of non-conducting material and the region of conducting material, the electrically conducting region presenting an area of electrically conducting material to a fluid flowing through the passage in use, and the electrically conducting material is electrically conducting diamond and the non-conducting material is non-conducting diamond.

39. A method comprising:
processing a fluid either as part of an analysis or as an alternative to the analysis by a microelectrode,
wherein the microelectrodes comprises a body formed from electrically non-conducting material and including at least one region of electrically conducting material and at least one passage extending through the body of non-conducting material and the region of conducting material, the electrically conducting region presenting an area of electrically conducting material to a fluid flowing through the passage in use, and the electrically conducting material is electrically conducting diamond and the non-conducting material is non-conducting diamond.

40. A method comprising:
processing a fluid for use external to a microelectrode structure,
wherein the microelectrodes comprises a body formed from electrically non-conducting material and including at least one region of electrically conducting material and at least one passage extending through the body of non-conducting material and the region of conducting material, the electrically conducting region presenting an area of electrically conducting material to a fluid flowing through the passage in use, and the electrically conducting material is electrically conducting diamond and the non-conducting material is non-conducting diamond.

41. A method comprising:
modifying a fluid by electrical means by a microelectrode,
wherein the microelectrodes comprises a body formed from electrically non-conducting material and including at least one region of electrically conducting material and at least one passage extending through the body of non-conducting material and the region of conducting material, the electrically conducting region presenting an area of electrically conducting material to a fluid flowing through the passage in use, and the electrically conducting material is electrically conducting diamond and the non-conducting material is non-conducting diamond.

42. A method comprising:
modifying a fluid by electrochemical means by a microelectrode,
wherein the microelectrodes comprises a body formed from electrically non-conducting material and including at least one region of electrically conducting material and at least one passage extending through the body of non-conducting material and the region of conducting material, the electrically conducting region presenting an area of electrically conducting material to a fluid flowing through the passage in use, and the electrically conducting material is electrically conducting diamond and the non-conducting material is non-conducting diamond.

43. A method comprising:
modifying a fluid by means of mixing by a microelectrode,
wherein the microelectrodes comprises a body formed from electrically non-conducting material and including at least one region of electrically conducting material and at least one passage extending through the body of non-conducting material and the region of conducting material, the electrically conducting region presenting an area of electrically conducting material to a fluid flowing through the passage in use, and the electrically conducting material is electrically conducting diamond and the non-conducting material is non-conducting diamond.

44. A method comprising:
modifying a fluid by means of dispersion into liquid droplets suspended in a gas by a microelectrode,
wherein the microelectrodes comprises a body formed from electrically non-conducting material and including at least one region of electrically conducting material and at least one passage extending through the body of non-conducting material and the region of conducting material, the electrically conducting region presenting an area of electrically conducting material to a fluid flowing through the passage in use, and the electrically conducting material is electrically conducting diamond and the non-conducting material is non-conducting diamond.

* * * * *